(12) United States Patent
Glickman

(10) Patent No.: US 7,022,097 B2
(45) Date of Patent: Apr. 4, 2006

(54) METHOD FOR TREATING GLANDULAR DISEASES AND MALIGNANCIES

(76) Inventor: Morton Glickman, 28 Temple Ct., New Haven, CT (US) 06511

( * ) Notice: Subject to any disclaimer, the term of this patent is extended or adjusted under 35 U.S.C. 154(b) by 46 days.

(21) Appl. No.: 10/435,579

(22) Filed: May 9, 2003

(65) Prior Publication Data

US 2004/0225251 A1    Nov. 11, 2004

(51) Int. Cl.
*A61M 37/00*  (2006.01)
*A61M 5/00*   (2006.01)
*A01N 1/00*   (2006.01)
*A61B 19/00*  (2006.01)

(52) U.S. Cl. .......................... 604/4.01; 604/8; 604/5.01; 128/898; 435/1.1

(58) Field of Classification Search ............... 604/4.01, 604/5.01, 5.02, 5.04, 6.06, 6.09, 6.16, 500, 604/506–510, 96.01, 101.01, 101.03–101.05, 604/102.01, 103.03–103.05, 104, 522; 606/191, 606/192, 194, 195, 198; 436/64, 813, 824

See application file for complete search history.

(56) References Cited

U.S. PATENT DOCUMENTS

| 5,062,662 | A  | * | 11/1991 | Cameron ..................... 280/733 |
| 5,069,662 | A  | * | 12/1991 | Bodden ....................... 604/5.01 |
| 5,411,479 | A  |   | 5/1995  | Bodden |
| 5,817,046 | A  | * | 10/1998 | Glickman .................. 604/5.04 |
| 6,186,146 | B1 | * | 2/2001  | Glickman .................. 128/898 |
| 6,287,273 | B1 | * | 9/2001  | Allers et al. .................. 604/27 |

* cited by examiner

*Primary Examiner*—Patricia Bianco
(74) *Attorney, Agent, or Firm*—Stephen E. Feldman

(57) ABSTRACT

A method for the in situ treatment of diseases and malignancies in a living host body. The method includes exposing a diseased or malignant gland of a host body to an effective amount of a therapeutic agent by infusing the therapeutic agent into blood flowing from the diseased or malignant gland that has been captured and contained in an isolated section associated with the gland. The contaminated blood from this isolated section is then evacuated from the host body, cleaned, detoxified and returned to the host body without exposing other glands, organs or tissue of the host body to the contaminated blood and without interrupting the normal flow of blood circulating through the host body.

11 Claims, 3 Drawing Sheets

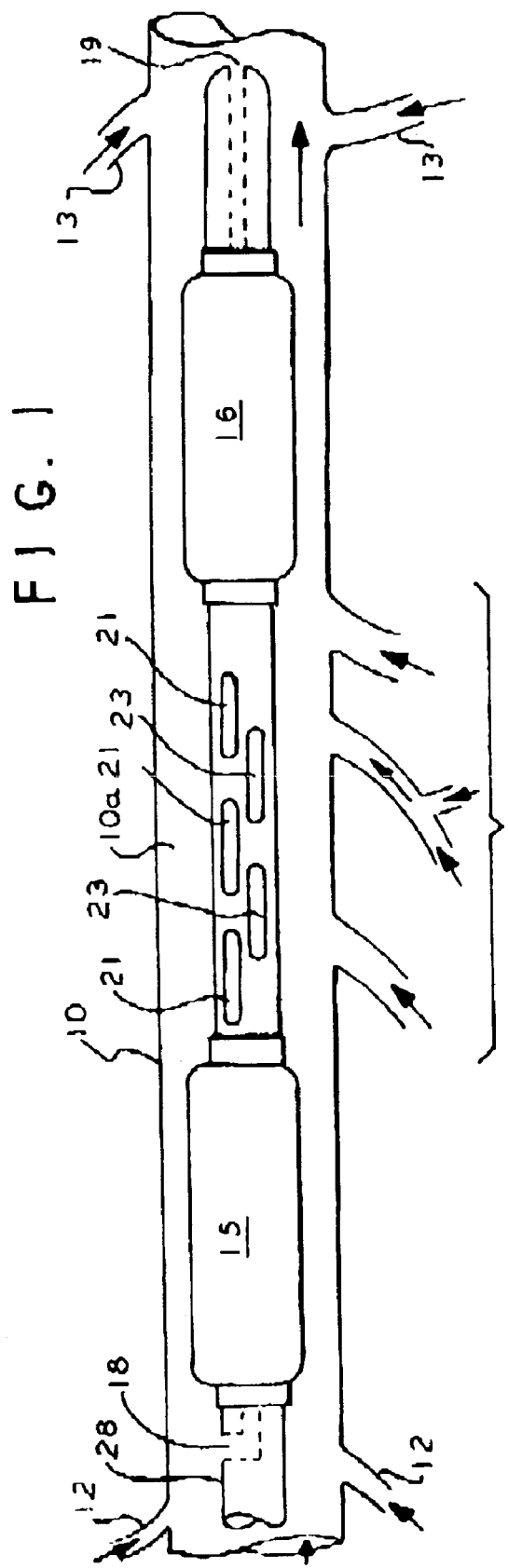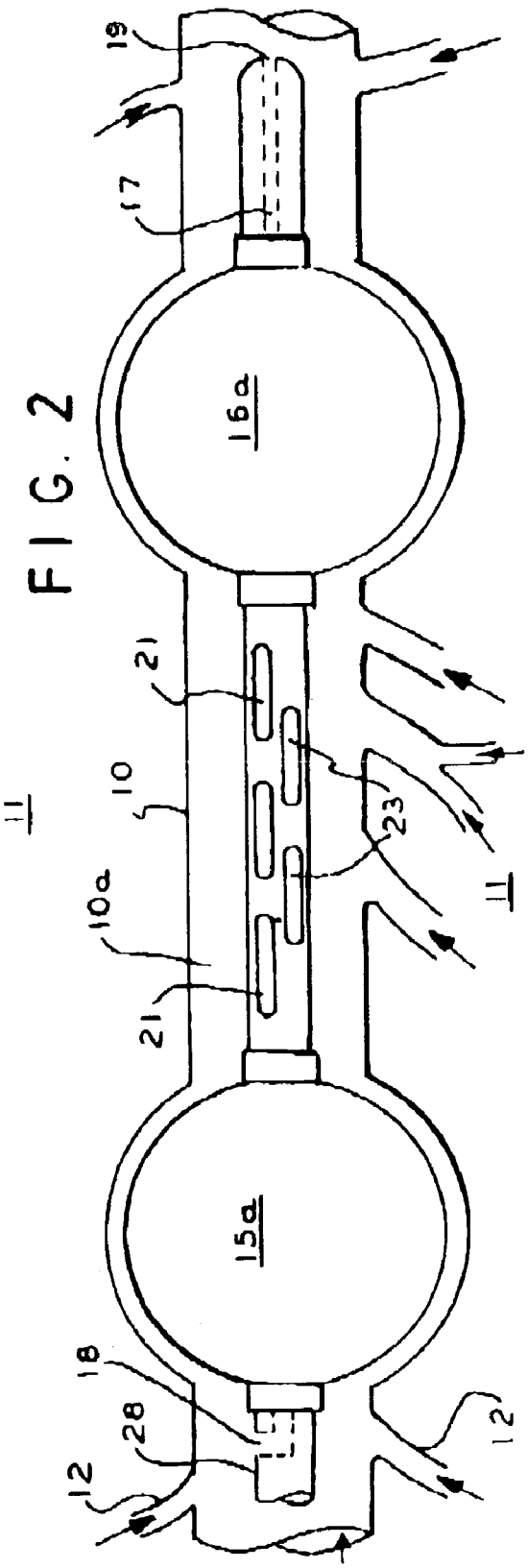

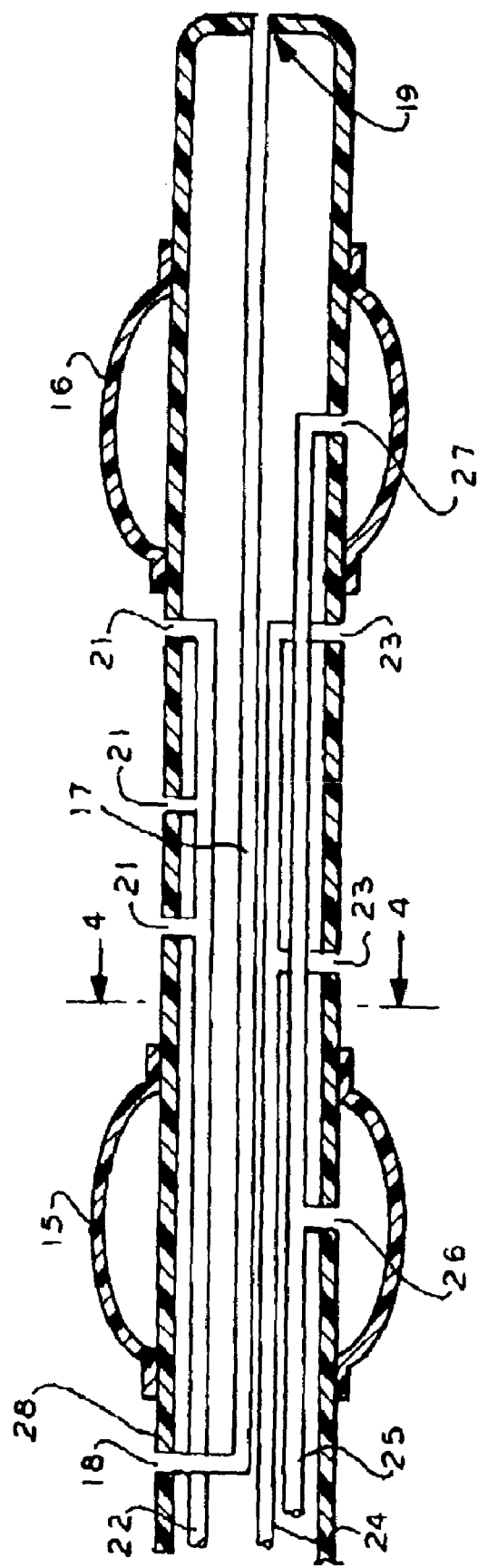

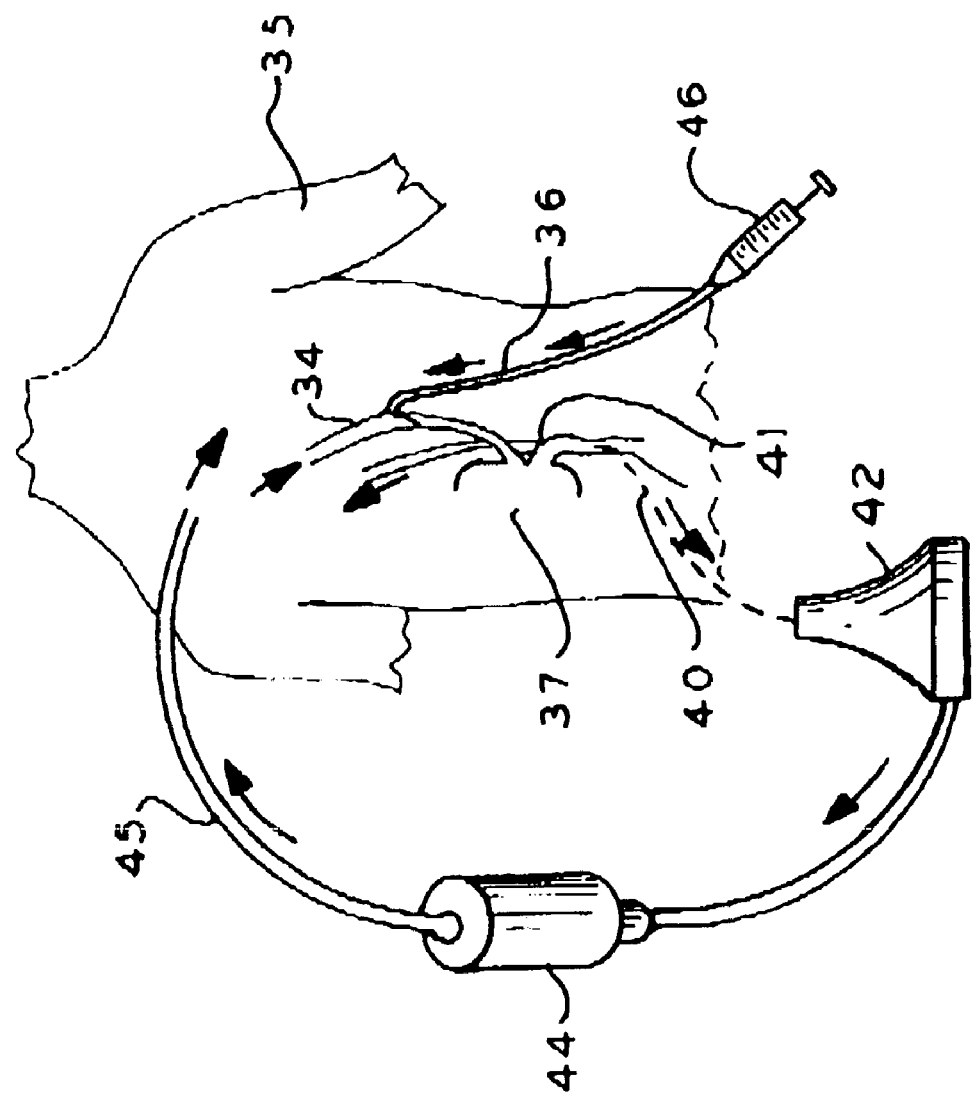
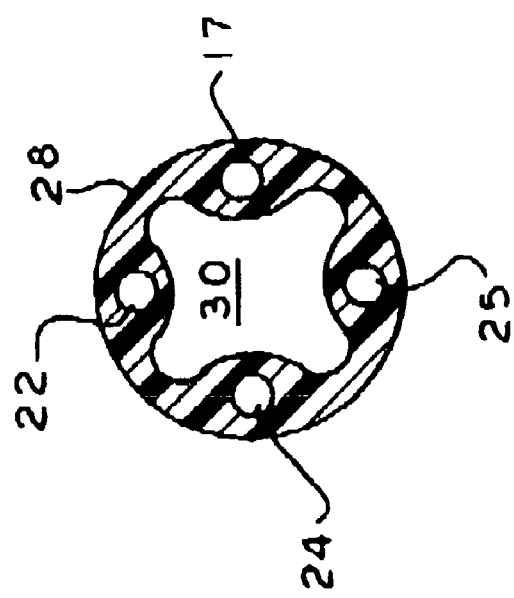

METHOD FOR TREATING GLANDULAR DISEASES AND MALIGNANCIES

FIELD OF THE INVENTION

This invention is directed to a method for treating glandular diseases and malignancies such as tumors and cancer in a human body. More particularly, the method of this invention includes isolating the diseased or malignant gland from the general circulation system of the body and treating the gland in situ without affecting other glands, organs or tissue of the body. Even more particularly, the method of this invention includes directly infusing the diseased or malignant gland with a therapeutic agent through the blood supplying the gland while eliminating contaminated blood from the affected gland and maintaining normal blood circulation throughout the body.

BACKGROUND OF THE INVENTION

Current acceptable medical practice for treating malignancies of body organs such as the kidney and the liver also involve surgical removal of the afflicted areas or, if the cancer is malignant, surgical removal of the entire organ. Since it is an organ that is involved and not a gland, about 20% to about 30% of the patients undergoing this form of therapy exhibit a sustained, favorable response.

Some organ malignancies have also been treated in situ with toxic agents such as chemotherapeutic agents and biological agents that are toxic moieties obtained from organic sources. However, it has been found that these agents can not generally be introduced into the main blood circulation of the body in sufficient strength and/or quantity to achieve desired therapeutic responses in the affected organs as their negative toxic effects on other organs and tissues of the body off-set their potential positive therapeutic effect in the afflicted organ.

Another method of treating malignant organs involves growing immune cells; i.e., Tumor Infiltrating Lymphocytic cells (TIL cells) within the affected organ in order to attack the cancerous tumors.

A further method of treating malignant organs involves the surgical removal of the cancerous tumors from the affected organ and cultivating TIL cells in sufficient quantity so that the cultivated cells can be infused beck into the patient for therapeutic treatment of the affected organ. However, this approach requires time to cultivate a sufficient quantity of the cells for adequate and effective treatment and the patient may not have the time necessary to benefit from this approach.

Although similar approaches have been used to treat diseases and malignancies of glands in living, human, host bodies, they have generally not been as successful as the treatments described above for treating organs of a host body. Treatment of diseases and malignancies of such glands as the thyroid, parathyroid and prostate with radiation or surgical removal have been generally successful, but leave the patient susceptible to adverse side affects. Treatment of diseases and malignancies of other glands such as the adrenals and pancreas is usually accomplished by surgical removal of the gland and the patient typically expires within a few months.

For example, treatment of diseases and malignancies of the pancreas by surgical removal is particularly troublesome as the surviving patient has a limited life span. The pancreas is located behind the stomach and comprises two portions: one portion secretes digestive juices which pass into the duedonum; the other portion secretes insulin which passes into the bloodstream. The pancreas can become afflicted with two major types of tumors: ductal adenocarcinoma and endocrine tumors that can be either non-functioning tumors or functioning tumors. Non-functioning tumors can result in obstruction of the bilary tract or the duedonum, bleeding into the GI tract or be evidenced as abdominal masses. Functioning tumors can cause severe symptoms such as hypoglycemia, Zolinger-Elison syndrome, hypokalemia, carcinoid syndrome, and the like.

When ductal adenocarcinoma is present, current treatment methods involve surgical removal of the affected areas it the cancer has not spread. Less than 2% of the patients undergoing this procedure survive for more than five years. When endocrine tumors are present, it is typical to surgically remove both the pancreas and the deudonum. In these instances, about 10% of the patients survive for five years.

It will be appreciated from the foregoing discussion that treating malignant or tumorous organs and glands of the body with chemotherapeutic agents has not had a significant affect. While certain drugs and biological agents have demonstrated some positive activity for a few treatments, these positive effects have been generally negated by systemic toxicity.

Processes for treating diseased tissues and organs of the body such as the liver and the kidney are known such as those disclosed in U.S. Pat. No. 6,186,146 B1 to Glickman; U.S. Pat. No. 5,411,479 to Bodden, and, U.S. Pat. No. 5,089,662 to Bodden, et.al. In general, these processes include the use of a double balloon catherer that is percutaneously inserted into the inferior vena cava of the affected organ to prepare it for the delivery of blood flowing between the organ and the heart. Blood vessels carrying blood from the organ are blocked by inflating the balloons in the catherer to prevent contaminated blood in the organ from entering the general circulation system of the body. The viscous blood from the organ contaminated with the therapeutic agent is then withdrawn from the body. The balloons in the double balloon catherer are positioned to span the vessels that carry the blood exiting from the organ and are expanded to block the vessels above and below the exit vessels to effectively isolate the blood flowing from the treated organ. The contaminated blood is removed from the body by means of an opening in a lumen provided in the catherer positioned between the expanded balloons. The contaminated blood is treated outside the body to remove the contaminants from it whereupon the cleaned, detoxified blood is returned to the general circulation system of the body.

SUMMARY OF THE INVENTION

The method of this invention treats a diseased gland of the body by stimulating a response in the diseased gland in situ by infusing a therapeutic agent into the gland via the blood entering the gland and recovering the blood containing the therapeutic agent and removing it from the gland before the contaminated blood enters the general circulation system of the body. This is accomplished by blocking a section of a major vein of the gland without interrupting the blood flowing through the major veins and through the general circulation system of the body.

In general, the method of the invention comprises exposing a diseased or malignant gland of the body to an effective amount of a therapeutic agent by infusing said agent into the blood entering said gland; creating an isolated section in a major vein that spans the area where tributary veins connect with said major vein, said major vein and said tributary veins being directly associated with said gland; passing contaminated effluent blood from the tributary veins of said gland to said isolated section and capturing said contaminated blood therein; positioning a shunt in said major vein that by-passes said isolated section so that blood is able to concurrently and continuously flow through said major vein, and, evacuating said captured blood from said isolated section without exposing other glands, organs or tissue of the body to said contaminated effluent blood and without interrupting the general blood circulation in the system of said body.

In one embodiment, the isolated section is formed by inserting a catherer having spaced apart expandable means into the major vein so that when the expandable means are expanded, the isolated section is created.

In another embodiment, the spaced apart expandable means prevents contaminated effluent blood from circulating to the heart of a body.

In a further embodiment, the evacuated, contaminated blood is withdrawn from the host body, cleaned, detoxified and then returned to the general circulation system of the host body.

The method of the invention can be readily used to treat such glands of the body as the adrenals, pancreas, prostate, thyroid and parathyroid of a living host body and is particularly useful to treat diseases and malignancies of the pancreas.

A significant and important advantage of the method of the invention over currently practiced protocols is that the toxicity or strength of the therapeutic agent used to treat the diseased or malignant gland is limited only by the level that the treated gland can withstand rather than by the adverse affect that the agent may have on other glands, organs or tissues of the body. It is also significant and important to note that blood contaminated with the therapeutic agent that flows from the treated gland can be isolated, removed and evacuated from the body, detoxified and cleansed and then be returned to the body without disrupting, interrupting or stopping the normal circulation of blood flowing through the body.

As discussed above, current protocols to treat diseases and malignancies affecting the glands of the body include surgical removal of the diseased tissues of the gland, culturing the lymphocyte cells infiltrating the malignant tumors, i.e., Tumor Infiltrating Lymphocytes (TIL cells) to cultivate a sufficient amount of the TIL cells and potentiate the cytolytic activity of these cells prior to infusing them into the body of a patient for treatment.

This approach requires that IL-2 be used in sufficient quantity in the culture medium to expand and activate the TIL cells. It typically takes from about four to about six weeks to cultivate a sufficient number of cells to treat a patient. After a sufficient number of cells have been cultivated, they are placed in a transfusion device for delivery to a patient. As these cells are delivered to a patient, the patient also receives bolus injections of IL-2 every eight hours for five continuous days. This treatment protocol is commonly referred to as TIL/IL-2 therapy.

Since it is not always possible to provide a sufficient amount of cells to effectively treat a patient, TIL/IL-2 therapy is not always effective or successful. Cultivating an adequate supply of cells is labor intensive and expensive and can fail for many reasons relating to the cultivation conditions, the most common being contamination of the cell culture. Thus, each step of the cultivating process increases the likelihood of failure. When this occurs, precious time can easily be lost further delaying therapy, often discouraging a patient from undergoing another attempt.

The method of this invention permits IL-2 to be delivered directly to a diseased area or malignancy in the patient rather than removing a diseased area or malignancy from a patient for cell cultivation. Since the method of the invention permits high doses of IL-2 to be infused directly to a diseased area or malignancy, surgical procedures are not necessary, side effects of administered therapy, especially infection, are avoided and potential failure and subsequent delay of cell cultivation are eliminated. By using the method of the invention, the anti-tumor of the body's immune system is enhanced.

The method of the invention includes the insertion of a catherer into an artery feeding blood to a gland to be treated and infusing a therapeutic agent into the gland through the blood flowing into it. The catherer that can be used is one normally employed for such procedures. A second catherer containing a double balloon catherer having two, spaced apart inflatable balloons is inserted into a major vein of the circulation system and positioned therein so that the spaced balloons span that portion or section of the major vein where the tributary veins coming out of the gland connect with the major vein. The spaced balloons are then inflated so that they contact the inner wall of the major vein forming spaced blocks or plugs to effectively block the spanned portion within the major vein. This creates an isolated section in which blood entering the major vein from the treated gland can be captured and isolated from the rest of the general circulation system.

The method of the invention also employs a by-pass that shunts blood flowing in a major vein through and past the section in the major vein that is blocked by the inflated, spaced balloons thereby permitting blood to flow through the major vein while blood flowing into the major vein from the gland undergoing therapeutic treatment is isolated and contained within the blocked section. Thus, the by-pass serves as an internal conduit or lumen within the double balloon catherer with its ends extending and protruding beyond the ends of the double balloon section of the catherer. The protruding ends of the lumen each has an opening formed in them, one of which is anterior (or cephalod) to and the other of which is posterior (or cauded) of the isolated section created by the spaced, inflated balloons.

Just prior to or concurrently with inflating the balloons of the double balloon catherer after it has been positioned in the major vein, the shunt or by-pass can be opened to provide a blood flow path around the blocked section created by the inflated balloons enabling the normal flow of blood to be continued through the major vein without interruption.

Blood flowing from the treated gland into the isolated section formed between the inflated balloons and containing a contaminating therapeutic agent is evacuated from the isolated section by means of one or more internal conduits or lumens provided within the double balloon catherer that are positioned between the spaced balloons. The internal conduits or lumens have a plurality of openings formed in them and the ends of these lumens also extend beyond the ends of the double balloon catherer. This permits the contaminated blood to enter these lumens through their openings enabling the contaminated blood to be evacuated from the isolated section between the inflated balloons that are contained in the major vein via the protruding ends of the internal lumens. The protruding ends of the internal lumens are connected to an external blood cleansing apparatus that removes the contaminating therapeutic agent from the blood and then returns the cleaned and detoxified blood back into the general circulation system of the body.

The contaminated blood can be cleaned and detoxified by commercial means and techniques well known to the medical practitioner. These means and techniques include, among others, hemoperfusion cartridges, hemodialysis, hemofiltration, and hemoadsorption wherein antibodies, biological ligands, are used that are capable of detoxifying the blood. After the contaminating therapeutic agent has been removed from the blood, the cleaned, detoxified blood can be re-administered back into the patient Representative devices and apparatus that incorporate these techniques and means are disclosed in U.S. Pat. Nos. 4,820,261, 4,637,880; and, 4,362,155.

BRIEF DESCRIPTION OF THE DRAWING

The method of the invention will become more apparent from the ensuing description when considered together with the accompanying drawing wherein:

FIG. 1 is a side view illustrating a double balloon catherer with the balloons deflated and containing an internal blood shunt positioned in a blood vessel;

FIG. 2 is the same as FIG. 1 but showing the balloons in an inflated Condition;

FIG. 3 is a cross sectional view of the double balloon catherer shown in FIG. 2;

FIG. 4 is a view taken substantially on the line 4—4 of FIG. 3; and,

FIG. 5 is a schematic view illustrating the devices and apparatus that can be used in practicing the method of the invention.

DETAILED DESCRIPTION OF THE DRAWING AND THE INVENTION

Referring to the Figures of the drawing wherein like reference numerals denote like parts there is shown in FIGS. 1 and 2 a front end or head end portion of a double balloon catherer that is positioned in the blood vessel of a major vein 10 such as a section of a major vein. Blood vessel groups 11, 12 and 13 represent tributary veins that deliver blood to the major vein and then return blood to the heart. In this illustration, the group of tributary veins 11 represent those veins that carry blood from a gland such as the pancreas to a major vein while the other groups of tributary veins 12 and 13 represent those that deliver blood to the major vein from other parts of the body.

The catherer head end portion contains spaced apart inflatable balloons 15 and 16 which are shown in a deflated condition in FIG. 1 and in an inflated condition in FIG. 2 at 15a and 16a. When inflated to the condition shown in FIG. 2 at 15a and 16a, the outer surface of the inflated balloons 15 and 16 contact the interior wall of the major vein to form a blockage or isolated area 10a in the vein 10 in which the catherer has been positioned as illustrated in FIG. 2. This blocked and enclosed isolated area 10a spans the entry points of tributary veins 11 thereby capturing and containing blood entering the isolated area 10a created in the major vein from the tributary veins 11. This blockage interrupts the flow of blood through the major vein.

As shown in FIGS. 2 and 3, a blood shunt having an internal conduit or lumen 17 is contained within the double balloon catherer so that it is longitudinally co-extensive within the interior of the double balloon catherer between the extremities of balloons 15 and 16 thereby providing a by-pass for the flow of blood. A plurality of openings 18 and 19 are formed in the outer ends of internal conduit or lumen 17 that extend beyond balloons 15 and 16. With this arrangement, the integrity of the isolated section 10a is guaranteed in the major vein while providing an alternate path for the flow of blood past the isolated section 10a to maintain a continuous and uninterrupted flow of blood through vein 10.

Well known and commonly accepted medical techniques and devices can be used to inflate and deflate balloons 15 and 16. Illustrative of such techniques and devices are those that are capable of supplying a fluid to and evacuating a fluid from the interiors of the balloons by means of a lumen 25 as illustrated in FIGS. 3 and 4. Ports 26 and 27 are formed in conduit or lumen 25 that communicate with the interiors of balloons 15 and 16. Conduit or lumen 25 is also disposed longitudinally co-extensive within the double balloon catherer with the outer end of conduit or lumen 25 connected to an external control 42 as shown in FIG. 5.

Additional conduits or lumens 22 and 24 can also be disposed longitudinally co-extensive within the double balloon catherer to its outer ends. These conduits or lumens 22 and 24 have a plurality of openings 21 and 23 formed therein that communicate with the interior of the double balloon catherer as shown in FIG. 3. Although conduits or lumens 22 and 24 can be used for either infusion or evacuation purposes, they are used, in practicing the method of this invention, to evacuate blood from the isolated section 10a of the major vein. Conduits or lumens/openings 21/22 and 23/24 can be used separately or in combination depending upon the viscosity of the blood flowing through the tributary veins 11. This arrangement permits blood captured and contained within the isolated section 10a to be evacuated therefrom through either openings 21 in conduit or lumen 22 and/or openings 23 in conduit or lumen 24 through the outer end of the double balloon catherer while permitting blood to flow through the major vein by means of blood shunt 17 and its ports 18 and 19.

The outer wall of the double balloon catherer is shown in FIG. 4 having internal conduits or lumens 17, 22, 24 and 25 positioned within it. The central, internal portion 30 of the double balloon catherer is open along its longitudinal length enabling a guide wire (not shown) to be inserted into the central portion 30 so that the double balloon catherer can be slid along its length when positioning the double balloon catherer in the circulation system as is typically practiced in current medical procedures.

In practicing the method of this invention, there is schematically illustrated in FIG. 5 conventional, external instrumentation associated with a host body 35. A catherer, such as those used to deliver or evacuate fluids to or from internal parts of the body through arteries or veins of the circulation system, is inserted into an artery 34 between the heart and the gland, such as the pancreas, 37 to be treated. To accomplish this, a small incision is made in the body 35 so that a medically acceptable guide wire can be inserted into the body and through an artery 34 in the opposite direction as the blood is flowing in the artery to the gland 37. This procedure is typically performed with observation through a fluoroscopic instrument.

Once the guide wire has been positioned, the outer end of the guide wire outside the body is placed into the open end of a catherer 36 which is then slid along the guide wire into the body and then through the artery until it is appropriately positioned in the artery so as to permit a therapeutic agent to be infused and delivered through the catherer and into the blood entering the gland 37. A therapeutic agent delivery means, such as syringe 46, is connected to the outer end of and communicates with the catherer in delivering a therapeutic agent to the gland 37 to be treated.

Another small incision is made in the host body 35 and a second guide wire is inserted into the body and fed along a major vein 41 in the same direction that blood is flowing in that vein to the gland 37 to be treated. After this second guide wire has been properly positioned, the outer end of the second guide wire is inserted into the open end of a rigid catherer having a tip that is tapered to a point so that it can be tightly fitted to the second guide wire. The body of the rigid caterer is encased in a tightly fitted, thin walled sheath and this catherer assemblage is then advanced into the vein over the second guide wire and the double balloon catherer is then urged along the second guide wire into the body through a major vein and positioned at the gland 37 to be treated.

In FIGS. 1 and 2, the major vein 10 with its associated tributary veins 11 represent a like section of the major vein 41 shown in FIG. 5 where the tributary 30 veins from the gland 37 to be treated connect with the major vein. In FIG. 5, the second catherer 40 represents the double balloon catherer with its interior blood shunt and its interior conduits and lumens as are illustrated in FIGS. 1, 2 and 3. Catherer 40 is inserted into a major vein 41 that is carrying blood from the gland 37 to be treated and from other parts of the body to the heart of the host body and is positioned substantially as shown in FIGS. 1 and 2 with balloons 15 and 16 spanning the tributary veins 11 that are carrying blood from the gland 37 to be treated to the major vein, When the double balloon catherer 40 is properly positioned in a major vein 41, it spans the tributary veins 11 from the gland 37 to be treated so that blood flowing from the gland 37 can be captured and contained in the isolated section 10a of the major vein 41 when balloons 15 and 16 are expanded to their inflated conditions 15a and 16a to create the isolated section 10a in the major vein 41 that contains the tributary veins 11.

The outer end of the double catherer 40 is connected to a control 42 that is capable of inflating and deflating balloons 15 and 16. Control 42 also includes a means for evacuating blood from the isolated section 10a by means of internal conduits or lumens 22 and 24 and their associated openings 21 and 23, respectively. Blood evacuated from the isolated section 10a is then fed to a filtering device 44 that is equipped with means to remove contaminants and toxins from the blood. Filtering device 44 then returns the cleaned decontaminated and detoxified blood to the host body via a conduit 45 that is inserted into the general circulation system of the body 35.

Prior to or concurrently with introducing a therapeutic agent through catherer 36 via delivery means 46, control 42 is activated to expand balloons 15 and 16 in the double balloon catherer 40 to their fully inflated condition 15a and 16a securely contacting and held against the interior wall of the major vein 41 (FIG. 3). Inflated balloons 15a and 16a form anterior and posterior blockages creating isolated section 10a that brackets or spans tributary veins 11 from gland 37 permitting effluent blood from the gland 37 to be captured and maintained in the isolated section 10a until subsequently evacuated. Although this blockage is formed in the major vein 41, blood is permitted to continuously flow through the major vein 41 from the gland 37 by means of the blood shunt spanning the blocked portion of the major vein.

In practicing the method of the invention, a therapeutic agent such as a biological agent or IL-2 can be infused into the gland 37 to be treated with the blood flowing into the gland After being contaminated with the therapeutic agent, this blood can then be isolated and captured and then be subsequently evacuated from the body, cleaned and detoxified and then returned to the body. During this time, normal blood continues to flow through the rest of the body by means of the blood shunt by-pass.

When complicated geometries of the major vein 10 and tributary vessels 11 are encountered, more than one catherer can be used to accommodate and overcome these complications. For example, separate catherers can be employed to accomplish isolation and evacuation or shunt means for transporting blood past the isolated section of the vein. For example, a second catherer can be used to block the blood flow through the branch of a vessel that extends from the isolated section. Similarly, more than one catherer 36 can be used to infuse a therapeutic agent into a gland or a group of glands that have more than one source of arterial blood supply.

Although the invention has been described with particularity and in some detail, it will be appreciated by those skilled in this art that changes and modifications can be made therein without departing from the scope and spirit of the invention.

What is claimed:

1. A method for treating in situ diseases and malignancies in a gland of a living host body comprising:
   (a) exposing a diseased or malignant gland of a host body to an effective amount of a therapeutic agent by infusing said agent into the blood entering said gland;
   (b) creating an isolated section in a major vein that spans the area where tributary veins connect with said major vein, said major vein and said tributary veins being directly associated with said gland;
   (c) passing contaminated effluent blood from the tributary veins of said gland to said isolated section and capturing said contaminated blood therein;
   (d) positioning a shunt in said major vein that by-passes said isolated section enabling blood to flow concurrently and continuously through said major vein; and,
   (e) evacuating said contaminated, captured blood from said isolated section without exposing other glands, organs or tissue of said host body to said contaminated effluent blood and without interrupting the general blood circulation in the system of said host body.

2. The method of claim 1 wherein said isolated section is formed by inserting a catherer into said major vein, said catherer having spaced apart expandable means capable of creating said isolated section.

3. The method of claim 2 wherein one of said spaced apart expandable means prevents said contaminated effluent blood from circulating to the heart of said host body.

4. The method of claim 1 wherein said gland is a member selected from the group consisting of the adrenals, the prostate, the thyroid and the parathyroids.

5. The method of claim 1 wherein said evacuated, contaminated blood is cleaned, detoxified and returned to the general blood circulation system of the host body.

6. A method for treating in situ diseases and malignancies in a gland of a living host body comprising:
   (a) exposing a diseased or malignant gland of a host body to an effective amount of a therapeutic agent by infusing said agent into the blood entering said gland, said gland being a member selected from the group consisting of the adrenals, the prostate, the thyroid and the parathyroids;
   (b) creating an isolated section in a major vein that spans the area where tributary veins connect with said major vein, said major vein and said tributary veins being directly associated with said gland and said isolated section being formed by inserting a catherer into said major vein, said catheter having spaced apart expandable means capable of creating said isolated section;

(c) passing contaminated effluent blood from the tributory veins of said gland to said isolated section and capturing said contaminated blood therein;

(d) positioning a shunt in said major vein that by-passes said isolated section enabling blood to flow concurrently and continuously through said major vein, and, (e) evacuating said contaminated, captured blood from said isolated section without exposing other glands, organs or tissue of said host body to said contaminated effluent blood and without interrupting the general blood circulation in the system of said host body.

7. The method of claim 6 wherein one of said spaced apart expandable means prevents said contaminated effluent blood from circulating to the heart of said host body.

8. The method of claim 6 wherein said evacuated, contaminated blood is cleaned, detoxified and returned to the general blood circulation system of the host body.

9. A method for treating in situ diseases and malignancies in the adrenals, the prostate, the thyroid and the parathyroid of a living host body comprising:

(a) exposing one of a diseased or malignant adrenals, prostate, thyroid and parathyroid of a host body to an effective amount of a therapeutic agent by infusing said agent into the blood entering one of said adrenals, prostate, thyroid and parathyroid;

(b) creating an isolated section in a major vein that spans the area where tributory veins connect with said major vein, said major vein and said tributary veins being directly associated with one of said adrenals, prostate, thyroid and parathyroid and said isolated section being formed by inserting a catherer into said major vein, said catherer having spaced apart expandable means capable of creating said isolated section;

(c) passing contaminated effluent blood from the tributory veins of one of said adrenals, prostate, thyroid and parathyroid to said isolated section and capturing said contaminated blood therein;

(d) positioning a shunt in said major vein that by-passes said isolated section enabling blood to flow concurrently and continuously through said major vein; and, (e) evacuating said contaminated, captured blood from said isolated section without exposing other glands, organs or tissue of said host body to said contaminated effluent blood and without interrupting the general blood circulation in the system of said host body.

10. The method of claim 9 wherein one of said spaced apart expandable means prevents said contaminated effluent blood from circulating to the heart of said host body.

11. The method of claim 9 wherein said evacuated, contaminated blood is cleaned, detoxified and returned to the general blood circulation system of the host body.

* * * * *